US007465555B2

(12) United States Patent
Anderson et al.

(10) Patent No.: US 7,465,555 B2
(45) Date of Patent: Dec. 16, 2008

(54) EARLY DETECTION OF SEPSIS

(75) Inventors: Stephen J. Anderson, The Woodlands, TX (US); Douglas J. Haney, Santa Clara, CA (US); Cory A. Waters, Pleasanton, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 614 days.

(21) Appl. No.: 10/400,275

(22) Filed: Mar. 26, 2003

(65) Prior Publication Data

US 2003/0194752 A1 Oct. 16, 2003

Related U.S. Application Data

(60) Provisional application No. 60/370,115, filed on Apr. 2, 2002.

(51) Int. Cl.
*G01N 33/00* (2006.01)
*G01N 33/53* (2006.01)
*G01N 33/532* (2006.01)
*G01N 33/566* (2006.01)
*G01N 33/567* (2006.01)

(52) U.S. Cl. .................. 435/7.24; 435/7.1; 435/7.2; 435/7.21; 435/7.92

(58) Field of Classification Search .................. 435/7.1, 435/7.21, 7.24, 7.92
See application file for complete search history.

(56) References Cited

U.S. PATENT DOCUMENTS

| 5,426,181 | A | | 6/1995 | Lee et al. | |
|---|---|---|---|---|---|
| 5,484,705 | A | | 1/1996 | White et al. | |
| 5,566,249 | A | * | 10/1996 | Rosenlof et al. | ............. 382/257 |
| 5,639,617 | A | | 6/1997 | Bohuon | |
| 5,780,237 | A | | 7/1998 | Bursten et al. | |
| 5,804,370 | A | * | 9/1998 | Romaschin et al. | ............. 435/5 |
| 5,830,679 | A | | 11/1998 | Bianchi et al. | |
| 6,077,665 | A | * | 6/2000 | Weirich et al. | ................. 435/6 |
| 6,190,872 | B1 | | 2/2001 | Slotman | |
| 6,303,321 | B1 | | 10/2001 | Tracey et al. | |
| 2001/0041177 | A1 | * | 11/2001 | Guyre et al. | ............. 424/130.1 |

FOREIGN PATENT DOCUMENTS

| RU | 2072103 | 1/1997 |
|---|---|---|
| SU | 1504597 | 8/1989 |
| WO | WO 03084388 A2 * | 10/2003 |

OTHER PUBLICATIONS

Baker et al., "In biomarkers we trust?", Nature Biotechnology, 2005, vol. 23, pp. 297-304.*
Bast, Jr, et al., "Translational crossroads for biomarkers", Clin. Cancer Res., 2005, vol. 11, pp. 6103-6108.*
Labaer, "So, you want to look for biomarkers (Introduction to the special biomarkers issue)", J. Proteome Res., 2005, vol. 4, pp. 1053-1059.*
Statsoft, Inc., 1999, Electronic Statistics Textbook, Tulsa, OK, http://www.statsoft.com/textbook/stathome.html.*
Davis, "Quantitative neutrophil CD64 expression: Promising diagnostic indicator of infection or systemic acute inflammatory response," 1996, vol. 16, pp. 121, 124-130.*
Knaus, W.A. et al, "The APACHE III Prognostic System*—Risk Prediction of Hospital Mortality for Critically Ill Hospitalized Adults", *Chest*, 100(6):1619-1636 (1991).
Bone, R.C. et al, "Definitions for Sepsis and Organ Failure", *Critical Care Medicine*, 20(6):724-726 (1992).
Cheadle, W.G., "The Human Leukocyte Antigens and Their Relationship to Infection", The *American Journal of Surgery*, 165(2A Suppl): 75S-81S (1993).
Roumen, Rudi M.H. et al, "Scoring Systems and Blood Lactate Concentrations in Relation to the Development of Adult Respiratory Distress Syndrome and Multiple Organ Failure in Severely Traumatized Patients", *The Journal of Trauma*, 35(5):349-355 (1993).
Wakefield, C.H., et al, "Changes in Major Histocompatibility Complex Class II Expression in Monocytes and T cells of Patients Developing Infection after Surgery", *British Journal of Surgery*, 80(2); 205-209 (1993).
Wakefield, C.H., et al, "Polymorphonuclear Leukocyte Activation-An Early Marker of the Postsurgical Sepsis Response", *Arch Surgery* , 128:390-395 (1993).
Sauaia, et al, "Early Predictors of Postinjury Multiple Organ Failure", *Arch Surgery*, 129:39-45 (1994).
Wagner, D.P., et al, "Daily Prognostic Estimates for Critically Ill Adults in Intensive Care Units: Results from a Prospective, Multicenter, Inception Cohort Analysis", *Critical Care Medicine*, 22(9):1359-1372 (1994).
Rangel-Frausto, M.S., et al, "The Natural History of the Systemic Inflammatory Response Syndrome (SIRS)", *Journal of the American Medical Association*, 273(2):117-123 (1995).
Asadullah, K., et al, "Immunodepression following Neurosurgical Procedures", *Critical Care Medicine*, 23(12):1976-1983 (1995).
Wakefield, C.H., et al, "Surgery and the Release of a Neutrophil Fcγ Receptor", *The American Journal of Surgery*, 170:277-284 (1995).
Rixen, D., et al, "Sepsis/SIRS, Physiologic Classification, Severity Stratification, Relation to Cytokine Elaboration and Outcome Prediction in Posttrauma Critical Illness", *The Journal of Trauma: Injury, Infection, and Critical Care*, 41(4):581-598 (1996).
Slotman, G.J., et al, "Multivariate Regression Modeling for the Prediction of Inflammation, Systemic Pressure, and End-organ Function in Severe Sepsis", *Shock*, 8(3):225-231 (1997).
Van Den Berk, J.M.M., et al, "Low HLA-DR Expression on Monocytes as a Prognostic Marker for Bacterial Sepsis After Liver Transplantation", *Transplantation*, 63(12):1846-1848 (1997).
Giannoudis, P.V., et al, "Stimulation of inflammatory markers after blunt trauma", *British Journal of Surgery*, 85:986-990 (1998).
Millili, J.J., et al, "Predicting Surgical Outcome Using Bayesian Analysis", *Journal of Surgical Research*, 77:45-49 (1998).

(Continued)

*Primary Examiner*—Unsu Jung
(74) *Attorney, Agent, or Firm*—Douglas A. Petry

(57) ABSTRACT

Diagnostic methods, systems, and kits for identifying patients with systemic inflammatory response syndrome who are likely to progress to sepsis.

3 Claims, 1 Drawing Sheet

OTHER PUBLICATIONS

Figure 1:
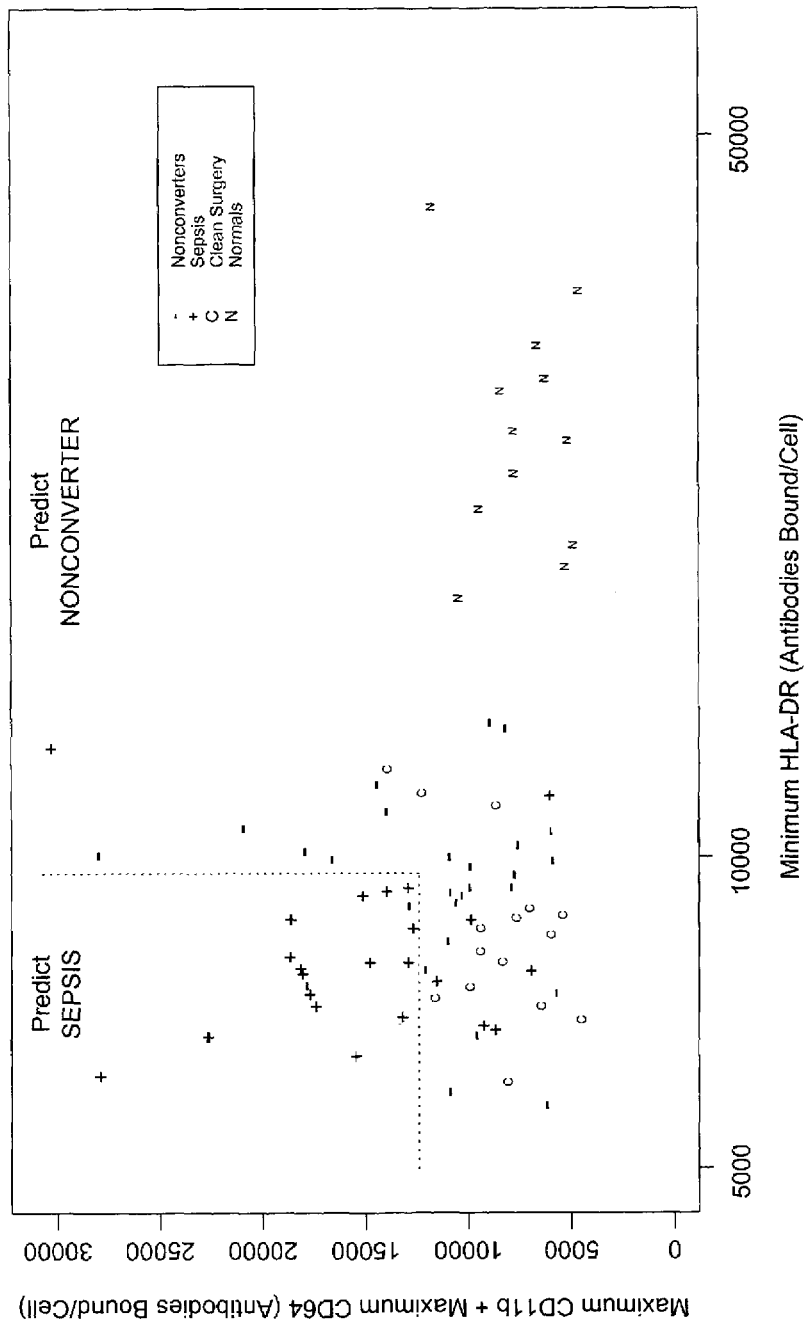

Rangel-Frausto, M.S., et al, "The Dynamics of Disease Progression in Sepsis: Markov Modeling Describing the Natural History and the Likely Impast of Effective Antisepsis Agents", *Clinical Infectious Diseases*, 27:185-190 (1998).

Weirich, E., et al, "Neutrophil CD11b Expression as a Diagnostic Marker for Early-onset Neonatal Infection", *The Journal of Pediatrics*, 132(ss.3,1):445-451 (1998).

De Bont, E.S.J.M., et al, "Plasma IL-8 and IL-6 Levels can be used to Define a Group with Low Risk of Septicaemia Among Cancer Patients with Fever and Neutropenia", *British Journal of Haematology*, 107:375-380 (1999).

Ditschkowski, M., et al, "HLA-DR Expression and Soluble HLA-DR Levels in Septic Patients After Trauma", *Annals of Surgery*, 229(2):246-254 (1999).

Taniguichi., et al, "Change in the Ratio of Interleukin-6 to Interleukin-10 Predicts a Poor Outcome in Patients with Systemic Inflammatory Response Syndrome", *Critical Care Medicine*, 27(7):1262-1264 (1999).

Takala, A., et al, "Systemic inflammatory response syndrome without systemic inflammation to acutely ill patients admitted to hospital in a medical emergency", *Clinical Science*, 96:287-295 (1999).

Manjuck, J., et al, "Decreased response to recall antigens is associated with depressed costimulatory receptor expression in septic critically ill patients", *Journal Laboratory Clinical Medicine*, 135(2):153-160 (2000).

Müller, B., et al, "Calcitonin precursors are reliable markers of sepsis in a medical intensive care unit", *Critical Care Medicine*, 4:977-983(2000).

Selberg, O, et al, "Discrimination of sepsis and systemic inflammatory response syndrome by determination of circulating plasma concentrations of procalcitonin, protein complement 3a, and interleukin-6", *Critical Care Medicine*, 28(8):2793-2798 (2000).

Slotman, G.J., "Prospectively validated predictions of shcok and organ failure in individual septic surgical patients: the Systemic Mediator Associated Response Test" *Critical Care*, 4(5) (2000) 319-326.

Nupponen, I, et al, "Neutrophil CD11b Expression and Circulating Interleukin-8 as Diagnostic Markers for Early-Onset Neonatal Sepsis", *Pediatrics*, 108(1):1-6 (2001).

Slotman, G.J., "Prospectively validated prediction of physiologic variables and organ failure in septic patients: The Systemic Mediator Associated Response Test (SMART)", Critical Care Medicine, 30(5):1035-1045 (2002).

Oczenski, W., et al. "HLA-DR as a Marker for Increased Risk for Systemic Inflammation and Septic Complications after Cardiac Surgery", Intensive Care Medicine, 29:1253-1257 (2003).

Perry, S.E. et al, "Is Low Monocyte HLA-DR Expression Helpful to Predict Outcome in Severe Sepsis?", *Intensive Care Medicine*, 29:1245-1252 (2003).

Muller Kobold et al., 2000, "Leukocyte activation in sepsis: Correlations with disease state and mortality," Intensive Care Medicine, vol. 26: 883-892.

* cited by examiner

Classification Tree for CD64, CD11b and HLA-DR

EARLY DETECTION OF SEPSIS

This application claims priority under 35 U.S.C. § 119(e) of provisional application Ser. No. 60/370,115, filed Apr. 2, 2002, which is incorporated herein by reference.

BACKGROUND OF THE INVENTION

1. Field of the Invention

The present invention relates to methods and reagents for identifying patients at risk for developing a systemic inflammatory condition, such as sepsis.

2. Description of Related Art

Early detection of the presence of disease conditions in patients typically allows more effective therapeutic treatments and results in more favorable clinical outcomes than occur when disease conditions are not recognized until an advanced stage. Unfortunately, the early detection of disease symptoms in many instances is problematic, and a disease may be relatively advanced before clinical suspicion of the disease occurs.

Systemic inflammatory conditions represent one class of diseases for which early diagnosis is particularly desirable, with sepsis being the most serious, and perhaps the most difficult to clinically diagnose. Sepsis is the result of the interaction of a pathogenic microorganism with a host's defense system that leads to systemic inflammation. Characterizing sepsis in a host, however, is made very complex by the number and heterogeneity of factors that play into the final outcome. The presence of underlying disease, a patient's genetically determined response to inflammatory stimuli, the general status of his/her immune system, and the microbial mediators and virulence factors released by infectious organisms, among other factors, all contribute to the disease course. The process by which this occurs is often remarkably rapid, leaving the clinician with little time to make a considered clinical judgment.

More significant yet is the high morbidity and mortality associated with sepsis. The incidence of sepsis has been increasing in the last 20 years and current figures indicate the presence of 750,000 cases per year of severe sepsis in the United States alone (Angus, D C et al. *Crit. Care Med.* 29:1303-1310 [2001]). The estimated crude mortality is 35%, all comorbidities being considered (Rangel-Frausto, M S. *Infectious Disease Clinics of North America* 13(2):299-312 [1999]). Sepsis is the 10$^{th}$ leading cause of death in the United States, and among hospitalized patients in noncoronary intensive care units, has been reported to be the most common cause of death. The disease accounts for an estimated $16 billion in annual health care expenditures in the United States alone. For the clinical practitioner, these epidemiologic and economic statistics place a high premium on making a correct and rapid clinical judgment in an arena where the clinician frequently has little more at his/her disposal than broad, non-specific clinical guidelines fortified by his or her own clinical experience.

Diagnosing sepsis at a point in time when the clinician can intervene with preventive measures has been and continues to be a very challenging task. Investigators point out that disease definitions that are too broad limit the ability of clinicians to direct appropriate therapies at patients who are at high risk for developing sepsis. In addition, these definitions do not permit the clinician to differentiate between an at risk patient who may derive a net benefit from a new, expensive therapy and a patient who will either not benefit, given his/her underlying disease co-morbidities, or who may be placed at higher risk from the therapy's inherent safety profile.

Sepsis typically results from the spread of a localized nidus of infection to the systemic circulation. Under these conditions, beneficial local inflammatory processes, mediated by specialized white blood cells such as neutrophils and monocytes and the factors they produce, and which are normally present to control the spread of the infectious focus, may expand their spheres of activity into life-threatening systemic inflammation. The course by which a patient progresses either to death or hospital discharge is well-known and has been described as a continuum from a state termed systemic inflammatory response syndrome (SIRS) to successive states of sepsis, severe sepsis, septic shock, multiple end-organ failure (MODS) and death (Rangel-Frausto, M S. *JAMA* 11:117-123 [1995]).

As a result of a recent consensus conference sponsored by the American College of Chest Physicians (*Crit. Care Med.* 20:864-874 [1992]), a uniform set of definitions for states associated with the sepsis syndrome was proposed. Systemic inflammatory response syndrome or SIRS is considered the accepted term for a clinical state in which two or more of the following clinical parameters are present: body temperature >38° C. or <36° C.; heart rate >90 beats/minute; respiratory rate >20 breaths/minute, or a $P_{CO2}$<32 mm Hg; and white blood cell count >12,000/mm$^3$, <4000/mm$^3$, or having >10% immature band forms. Sepsis is understood to be SIRS with a confirmed infectious process (positive culture). Severe sepsis is sepsis associated with organ dysfunction, hypoperfusion abnormalities, or hypotension. Hypoperfusion abnormalities include, but are not limited to, lactic acidosis, oliguria and mental status changes. Septic shock is understood to be sepsis-induced hypotension resistant to fluid resuscitation, and, having, in addition, the presence of hypoperfusion abnormalities.

Part of the challenge of classifying patients as septic is documenting the presence of a clinically significant microorganism. This is typically performed by culturing the patient's blood, sputum, urine, wound secretions, in-dwelling line surfaces, etc. Because many microorganisms require specialized conditions to promote their rapid growth, and may be more commonly present in certain body microenvironments, and because microbe numbers may initially be low at the site of infection, cultures are not always positive, even when a microorganism may be present. Thus, blood cultures, for example, may be positive only 17% of the time in patients that present with the clinical manifestations of sepsis (Rangel-Frausto, M S et al. *JAMA* 273: 117-123 [1995]). Moreover, cultures can also be inadvertently contaminated with microorganisms that are generally known to be non-pathogenic. In a study of 843 episodes of positive blood cultures from 707 patients with septicemia, only 12.4% of the coagulase-negative class of Staphylococci, for example, were clinically significant (Weinstein, M P et al. *Clinical Infectious Diseases* 24: 584-602 [1997]). Because of the difficulty of obtaining positive clinically significant cultures, investigators have defined culture-negative sepsis as SIRS with administration of empiric antibiotics under conditions where an infection is suspected but not confirmed by cultures (Rangel-Frausto, M S et al. *JAMA* 273: 117-123 [1995]).

The very complexity of the process of sepsis and the lack of clinically-relevant animal models have not only hampered the clinical community's ability to develop consensus definitions around the disease's characteristics, but have also slowed the pace of pharmaceutical progress in the field. Investigators point out that the field of sepsis clinical research has suffered from a long series of failed clinical trials that attempted to evaluate new treatment methodologies. The reasons why these trials failed are varied but one common theme that emerges is that many trial designs were based on animal model evidence that was of unknown clinical significance. Thus, because of differences between animal models of sepsis and human sepsis, for example, anti-inflammatory cytokine treatments may have been administered at a point in the patients' history when the patients were actually in a state of immune paralysis with undetectable levels of proinflammatory cytokines. In these settings, patients may not only fail to benefit from the treatment, but may be placed at increased risk from the treatment's inherent side effects, without the potential for an upside gain. The lack of ability to prospectively identify the patient cohort most likely to benefit from a therapy has hampered the implementation of rational timing and dosing regimens, and hence, outcomes have been dismal. Animal model experience, unfortunately, has not been a reliable guide for treatment timing and dosing regimens for humans (Opal, S M and Cross, A S. *Infectious Disease Clinics of North America* 13 (2): 285-297 [1999])

In addition to having consensus definitions, many clinicians would agree that what are most needed are assays to distinguish patients who display SIRS criteria, such as fever, and who will resolve without developing sepsis, from those patients who display SIRS criteria and who will progress to sepsis. In addition, other useful assays would identify patients who are most likely to benefit from a specific sepsis therapy, given existing comorbidities.

With respect to these points, most of the scoring systems and/or predictive models for sepsis that the clinician currently has at his/her disposal are oriented at, or utilized by, practitioners who intend to predict disease outcome in the patient who is already considered septic, and provide no indication of sepsis prior to its clinical onset. Reviewed by Roumen, R L et al. (*J. Trauma* 35: 349-355 [1993]), these scoring systems include the Injury Severity Score (ISS, 1974) which is a measure of the severity of blunt trauma injury to five major body systems, the Glasgow Coma Scale (SCS, 1974) which measures mental status changes, the Trauma Score (1980) which extends the Glasgow score to include respiratory and hemodynamic parameters, the TRISS method which combines physiologic and anatomic measurements to assess probability of surviving an injury, the Sepsis Severity Score (1983) which grades the functioning of seven body organs, the Polytrauma Score (1985) which adds an age parameter to the Injury Severity Score, the Multiple Organ Failure (MOF) Score (1985) which assesses the function of seven major organ systems and the APACHE II (1985). The latter is a comprehensive scoring system, which draws on data from a number of routinely measured physiological assessments in addition to a general health status score and an age score. APACHE, APACHE II, and its more recent version APACHE III, are typically used to predict the risk of death in certain groups of severely ill patients.

All of the aforementioned scoring systems, including the APACHE systems, show varying degrees of correlation with the outcomes of survival and death in sepsis patients. In a comparison of a number of these systems, Roumen, R M et al. (*J. Trauma* 35: 349-355 [1993]) concluded that the predictive value of a number of the severity scoring systems most appropriately addresses the identification of patients who will suffer late-stage complications of sepsis, not the presence or development of sepsis itself. Systems that measured physiologic response to trauma were not considered predictive as to late-stage outcome.

Various biological markers are known to be indicative of sepsis, and use of one or more biological markers to distinguish groups of patients who are septic from groups of patients who may have SIRS but are not septic has been reported. Many studies can be cited in which a group of septic patients is shown retrospectively to differ in its average level of a given marker from either a group of normal volunteers or a set of hospitalized controls. Other studies attempt to retrospectively differentiate groups of patients at various stages in the sepsis disease continuum from each other. Takala, A et al. (*Clin. Sci.* 96, 287-295 [1999], for example, have shown that groups of patients that are positive for two or more SIRS criteria can be distinguished from each other and from septic patients as well as from healthy controls by levels of selected biological markers. Based on each marker's levels in a given patient, a whole number subscore, known as the Systemic Inflammation Composite Score (SICS), is calculated. Statistically significant differences in SICS have been shown to exist between groups of patients with 2 positive SIRS criteria vs. 3 positive SIRS criteria vs. a group of septic patients. The SICS scoring system, however, is not intended to, and does not provide effective modeling for individual patients to detect when and if a given patient has become septic.

A method for the detection of septic shock and organ failure is described in Slotman, G J (*Critical Care* 4: 319-326 [2000]) and for systemic inflammatory conditions in general in U.S. Pat. No. 6,190,872. This method involves the daily measurement of selected biological markers in a model-building cohort of patients in an intensive care unit (ICU). A separate, unique predictive model is generated for each day of ICU stay. In constructing the model for a particular day, the same set of markers are used for each and every patient. However, models generated for different days may use different sets of markers. Each model applies to all patients who have been in the ICU the same number of days. This type of modeling fails to account for the variability in patient condition and rate of disease progression following admittance to the ICU. Furthermore, use of different models on each day makes it difficult to monitor patient progress.

SUMMARY OF THE INVENTION

The present invention provides methods, reagents, and kits for the detection of early sepsis. The present invention results from the discovery that an improved method of detecting patients who will progress to sepsis can be obtained by monitoring a plurality of suitable biological markers over a period time, independently deriving for each marker a statistical measure of extreme value of the marker over the period of time, and detecting early sepsis based on the combination of marker statistics.

Thus, the present invention provides methods of detecting early sepsis in a patient, comprising:
 a) monitoring a plurality of biological markers over a period of time,
 b) independently deriving for each marker a statistical measure of extreme value of the marker over the period of time, and
 c) applying a decision rule to the combined marker statistics to detect early sepsis in the patient.

A critical aspect of the present invention is the method of using the marker data obtained during monitoring. This aspect results from the discovery that consideration of the extreme marker values over the monitoring period may provide a better indicator of early sepsis than consideration of values obtained at one particular time, such as the most recently measured values alone. Thus, for each marker, a statistic that is a measure of the extreme value of a marker is calculated from the data for that marker accumulated over the interval of time that the patient is monitored and, furthermore, the statistic for each marker is calculated independently of the statistics for the other markers. This aspect of the invention distinguishes the present methods from methods that are based on the values of the monitored markers obtained at approximately the same time, as is the case, for example, in methods based on the current status of the patient. The present methods provide for the early detection of sepsis with greater sensitivity and specificity.

In a preferred embodiment, the methods are used as part of the process of monitoring SIRS patients, who are at risk of developing sepsis, for the impending onset of sepsis. A patient is monitored starting from the time that the patient is first identified to be at risk, most frequently upon becoming SIRS positive during an ICU stay following a surgical procedure. Following each measurement of the patient's markers during the course of monitoring, the detection criteria of the present methods will be applied to the data accumulated from both the previous and present measurements. Monitoring is continued until either the patient is identified as one who will progress to sepsis or the monitoring is discontinued.

Biological markers useful in the present methods are those that are informative of the state of the immune system in response to an infection or other severe clinical insult. Suitable markers include, for example, leukocyte count, cell surface markers, and soluble markers. In a preferred embodiment, the plurality of markers comprises at least one marker for a pro-inflammatory response and at least one marker for a compensatory anti-inflammatory response. Markers for a pro-inflammatory response include, for example, leukocyte count and cell-surface activation markers, such as adhesion molecules, including integrins, in particular, β2-integrins such as CD11b, and molecules in the Fc receptor family, including Fcγ receptors such as CD64. Markers for a compensatory anti-inflammatory response include markers of monocyte deactivation, such as MHC Class II molecules, in particular, HLA-DR and HLA-DQ. Other makers of either pro-inflammatory response or of compensatory anti-inflammatory response may be suitable, and can be selected following the teaching provided herein.

In a preferred embodiment, the plurality of biological markers comprises at least one marker for monocyte deactivation and at least one marker of neutrophil activation. Preferred markers of monocyte deactivation are the HLA Class II molecules expressed on peripheral blood cells, preferably, HLA-DR, and more preferably, monocyte-associated HLA-DR. Preferred markers of neutrophil activation include CD64 and CD11b, preferably, neutrophil-associated CD64 and neutrophil-associated CD11b.

The decision rule in the present methods is based on the extreme marker values over the monitoring period. In some embodiments, the statistical measure of extreme value is the maximum or minimum of the values obtained over the course of monitoring. Whether the maximum or minimum is measured depends on the marker. For example, decreased HLA-DR expression is a measure of monocyte deactivation and, thus, the minimum value of HLA-DR is most relevant in the present methods. Conversely, increased CD11b and CD64 are measures of a pro-inflammatory response, and the maximum values of these markers are most relevant.

In some embodiments, the statistical measure of extreme value is calculated directly from the set of data obtained for a marker. Alternatively, the set of data obtained first may be fitted to a curve, such as a polynomial or spline, and the statistical measure of extreme value is derived from the fitted curve. Such methods allow for interpolation of values in between data collection times and may increase detection sensitivity. Methods for fitting a curve to a set of points are well known in the literature.

The detection of sepsis is carried out using a decision rule applied to the marker statistics to classify patients as septic or non-septic. An optimal decision rule typically is generated from a controlled study in which a population of at-risk patients is monitored, and the subpopulation of patients who develop sepsis are compared to the subpopulation of patients who do not develop sepsis. The generation of a decision rule from a multivariate discrimination model is well known in the art and is described more fully, infra. In general, the resulting decision rule is a two-valued function of the data, which serves to identify the presence or absence of sepsis. However, multi-valued decision rules may be used that provide results interpretable as the likelihood that sepsis is present.

In a preferred embodiment, the plurality of makers comprises HLA-DR, CD11b, and CD64, and the statistics derived are the minimum HLA-DR expression, the maximum CD11b expression, and the maximum CD64 expression. Septic patients are identified using a decision tree based on these three statistics, preferably based on the minimum HLA-DR expression and the sum of the maxima of the CD11b and CD64 expressions. The threshold values of the decision tree are determined empirically, as described in the examples.

The present invention also provides kits useful for carrying out the present methods. The kits include a computer readable medium containing programming that implements the decision rule. In addition, the kits may include reagents, devices, and instructions for carrying out the monitoring of a patient's biological markers.

As discussed above, the course by which a patient progresses to death from sepsis is well-known and has been described as a continuum from a state termed systemic inflammatory response syndrome (SIRS) to successive states of sepsis, severe sepsis, septic shock, multiple end-organ failure (MODS), and death. The present methods enable the early detection of the progression from SIRS to sepsis, thereby enabling early intervention. It will be clear that, as the present methods enable the detection of sepsis prior to clinical suspicion, the present methods also enable the detection of any of these subsequent complications of sepsis prior to clinical suspicion.

BRIEF DESCRIPTIONS OF THE DRAWINGS

FIG. 1 provides a graphical representation of classification tree model analysis results for four groups of subjects, with (Maximum CD11b+Maximum CD64) shown on the vertical axis and with (Minimum HLA-DR) shown on the horizontal axis, for non-converter patients, sepsis patients, clean surgery patients and normal subjects. The decision thresholds are denoted by the dotted lines. The details of the analysis are described in Example 3.

DETAILED DESCRIPTION OF THE INVENTION

The following definitions are provided for reason of clarity, and should not be considered as limiting. Except where noted, the technical and scientific terms used herein are intended to have the same meaning as commonly understood by one of ordinary skill in the art to which the invention pertains.

As used herein, "systemic inflammatory response syndrome (SIRS)" refers to a clinical response to a variety of severe clinical insults, as manifested by two or more of the following:

temperature >38° C. (100.4° F.) or <36° C. (96.8° F.);

heart rate (HR) >90 beats/minute;

respiratory rate (RR) >20 breaths/minute, or $P_{CO2}$ <32 mmHg, or requiring mechanical ventilation; and white blood cell count (WBC) either >12.0×10$^9$/L or <4.0× 10$^9$/L or having >10% immature forms (bands);

within a 24 hour period. It is recognized that this represents a consensus definition of SIRS, and that the definition may be modified or supplanted by an improved definition in the future. The present definition is used herein to clarify current clinical practice, and does not represent a critical aspect of the invention.

As used herein, "SIRS patient" and "SIRS-positive patient" refer to a patient whose clinical presentation is classified as SIRS, as defined above, but who is not clinically deemed to be septic. SIRS patients in an ICU are considered to be at risk for progressing to sepsis.

As used herein, "sepsis" refers to a SIRS-positive condition associated with a confirmed infectious process.

As used herein, "culture-positive sepsis" refers to a sepsis in which the infectious process is confirmed by laboratory culture of a clinically significant organism(s). Visual inspection, however, is deemed sufficient for patients with perforated bowel and gross peritoneal soilage.

As used herein, "culture-negative sepsis" refers to sepsis in which the infectious process cannot be confirmed by laboratory culture of a clinically significant organism(s). Any non-culture confirmed visualization of potential infection, other than perforated bowel, is deemed culture-negative.

As used herein, "clinical suspicion of sepsis" refers to the suspicion that the SIRS-positive condition of a SIRS patient is due to an infectious process. In the context of the study reported herein, clinical suspicion also had to be high enough to warrant an order for cultures and administration of empiric antibiotics.

As used herein, "early sepsis" refers to an early stage in the onset of sepsis, prior to a stage when the clinical manifestations are sufficient to support a clinical suspicion of sepsis. The term "early sepsis" is a functional definition needed herein to refer to a previously un-named stage in the onset of sepsis. While not being constrained by the theory, it is believed that the present methods detect the initial indications of an infectious process, i.e., the initial indications of the onset of sepsis. However, because the present methods are used to detect sepsis prior to a time that sepsis is suspected using previously described methods, the patient's disease status at early sepsis can only be confirmed retrospectively, when the manifestation of sepsis is more clinically obvious. An alternative explanation is that the present methods detect immunological changes in a patient that either permit or facilitate the subsequent onset of an infectious process, resulting in sepsis. The exact mechanism by which a SIRS-positive patient becomes septic is not a critical aspect of the invention. Regardless of the mechanism, the methods of the invention detect initial indications that a patient will progress to sepsis, as classified by previously used criteria.

As used herein, "severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status.

As used herein, "septic shock" refers to sepsis-induced hypotension not responsive to adequate intravenous fluid challenge and with manifestations of peripheral hypoperfusion.

As used herein, "converter" or "converter patient" refers to a SIRS patient who progresses to clinical suspicion of sepsis during the period the patient is monitored, typically during an ICU stay.

As used herein, "non-converter" or "non-converter patient" refers to a SIRS-positive patient who does not progress to clinical suspicion of sepsis during the period the patient is monitored, typically during an ICU stay.

As used herein, "host compartment" refers to any portion, section, or sample obtainable from a patient or host from which biological markers may be obtained for measurement or evaluation. "Host compartments" include, by way of example and not of limitation, blood, serum, sputum, urine, and tissue biopsy samples.

As used herein, "marker" and "biological marker" refer to any biological compound derivable from a host compartment, or any physiological parameter measurable in a host, that is informative of the state of the patient, in particular, the immune system of the patient. A marker is considered to be informative if a measurable aspect of the marker is associated with the state of the patient. It will be understood that, for a particular molecule identified as a marker, the measurable aspect of the marker that is associated with the state of the patient may be, for example, the expression of, or level of expression of, the particular molecule.

As used herein, "statistic" or "statistical feature" refers to any function or, or summary measure derivable from, a set of marker data, or from modeled or smoothed values corresponding to these data.

As used herein, a "statistical measure of extreme value" refers to a statistic, calculated from the marker data measured over the monitored time period, that provides a measure of the extreme value of a marker over the monitored time period. Examples of a statistical measure of extreme value of the maker include a maximum or minimum of the marker level or of a fitted value over a time period, a maximum or minimum percent increase or decrease in marker measurements or in fitted values over a time period, a maximum or minimum time spent either above or below a threshold, a maximum or minimum level of variability of measurements or fitted values from two or more time points, a maximum or minimum slope of trend lines, a mean of possibly discontiguous local maxima or minima, and the like.

As used herein, "modeling a time series pattern" refers to creating a set of data points from marker measurements over a time period in which the measurements occur. In some instances, "modeling a time series pattern" will also include fitting a time series model or smoothing function to the measurements. Models used for fitting values to the time series measurements may include moving averages, autoregressions, locally weighted regressions (loess), B-splines, natural splines, and smoothing splines, as well as combinations of two or more these fitting techniques. These models are given by way of example and not of limitation, and other models will suggest themselves to those skilled in the art.

As used herein, "discrimination model" refers to a quantitative method for determining a decision rule for classifying patients. A "multivariate discrimination model" refers to any systematic method that uses measurements on two or more features or variables to assign cases to one of two or more groups, such as a group of patients with no disease and a group of patients with disease. These models are typically constructed from a data set that includes information on patient classification, and then, once constructed, are used to classify patients of unknown classification based on the patient measurements.

As used herein, "classification tree" refers to a model in which the data space is partitioned repeatedly into nested subsets, wherein each partitioning is based on a binary function of one or more measured parameters, in order to separate converter and non-converter patients. The model provides a decision tree in which each node (branch point) represents a binary decision point and the possible outcomes specify branches from the node. A patient is classified by proceeding through the tree, starting at the root, to a node, applying the binary test to the patient value, proceeding along the branch specified by test outcome, and repeating this process until the patient is assigned to a unique subset.

As used herein, "discriminant analysis" refers to a discrimination model in which a score is computed for each patient. The score is a linear function of the measured variables. Scores below a threshold are predicted to belong to one group, and scores above the threshold are predicted to belong to another group.

A "log-linear discriminant analysis" refers to a version of discriminant analysis in which measurements are transformed to the log scale prior to estimation of the coefficients for each measurement. In addition to the log transformation, any monotonic transformation may be used to create data distributions that are more Gaussian.

Statistical methods are well known in the art. Various commercially available computer programs, such as MICROSOFT ACCESS® 2000 database software, may be used for extraction of statistical features from stored, computer readable marker measurement data, and programs such as SPLUS® 2000 (MathSoft, Inc., Cambridge, Mass.) may be used to analyze the data.

Methods of the Invention

The present invention provides methods of detecting early sepsis in a patient, comprising the steps of:
d) monitoring a plurality of biological markers over a period of time,
e) independently deriving for each marker a statistical measure of extreme value of the marker over the period of time, and
f) applying a decision rule to the combined marker statistics to detect early sepsis in the patient.

Aspects of the methods are described in more detail, below.

Biological Markers

Biological markers useful in the present methods are, in general, those that are informative of the state of the immune system in response to an infection or other severe clinical insult, including, for example, leukocyte count, cell surface markers, and soluble markers. Biological markers may comprise any molecule or molecules obtainable from a patient, such as soluble or cell surface proteins, or any measurable physiological and/or clinical parameter, such as body temperature, respiration rate, pulse, age, blood pressure, white blood cell count, etc.

Biological markers that are informative of the state of the immune system in response to an infection include, by way of example and not of limitation, cell-surface proteins such as CD64 proteins, CD11b proteins, HLA Class II molecules, including HLA-DR proteins and HLA-DQ proteins, CD54 proteins, CD71 proteins, CD86 proteins, surface-bound tumor necrosis factor receptor (TNF-R), pattern-recognition receptors such as Toll-like receptors, soluble markers such as interleukins IL-1, IL-2, IL-4, IL-6, IL-8, IL-10, IL-11, IL-12, IL-13, and IL-18, tumor necrosis factor alpha (TNF-α), neopterin, C-reactive protein (CRP), procalcitonin (PCT), 6-keto F1α, thromboxane $B_2$, leukotrienes B4, C3, C4, C5, D4 and E4, interferon gamma (IFNγ), interferon alpha/beta (IFN α/β), lymphotoxin alpha (LTα), complement components (C'), platelet activating factor (PAF), bradykinin, nitric oxide (NO), granulocyte macrophage-colony stimulating factor (GM-CSF), macrophage inhibitory factor (MIF), interleukin-1 receptor antagonist (IL-1ra), soluble tumor necrosis factor receptor (sTNFr), soluble interleukin receptors sIL-1r and sIL-2r, transforming growth factor beta (TGFβ), prostaglandin $E_2$ ($PGE_2$), granulocyte-colony stimulating factor (G-CSF), interferon α/β, and other inflammatory mediators. Biological markers also include RNA and DNA molecules that encode or are otherwise indicative of the aforementioned protein markers.

In preferred embodiments, a plurality of markers is measured that comprises at least one marker for a pro-inflammatory response and at least one marker for a compensatory anti-inflammatory response. Markers for an pro-inflammatory response include, for example, leukocyte count and cell-surface activation markers, such as adhesion molecules, including integrins, in particular, β2-integrins such as CD11b, and molecules in the Fc receptor family, including Fcγ receptors such as CD64, and soluble markers such as CRP, PCT, IFNγ, LTα, IL-1β, IL-2, IL8, IL-12, IL-18, TNF-α, C', $LTB_4$, PAF, bradykinin, NO, GM-CSF, and MIF. Markers for a compensatory anti-inflammatory response include cell-surface markers of monocyte deactivation, such as MHC Class II molecules, in particular, HLA-DR and HLA-DQ, and soluble markers such as IL-1ra, sTNFr, sIL-1r, TGFβ, IL-4, IL6, IL-10, IL-11, IL-13, $PGE_2$, G-CSF, and IFN α/β.

In a preferred embodiment, the plurality of biological markers comprises at least one marker for neutrophil activation and at least one marker of monocyte deactivation. Increased expression of CD64 and CD11b is recognized as a sign of neutrophil and monocyte activation. Preferred cell-surface markers of neutrophil activation include CD64 and CD11b expressed on neutrophils. Preferred cell-surface markers of monocyte deactivation are the HLA Class II molecules expressed on peripheral blood cells, preferably, HLA-DR expressed on monocytes.

Each of the markers discussed above is known to change in response to an infection and may therefore be useful as a marker for an inflammatory condition. Various other biological markers that are indicative of an inflammatory condition are known to those skilled in the art and will suggest themselves upon review of this disclosure. It is expected that not all markers that are informative of the state of the immune system in response to an infection are equally informative. Consequently, the sensitivity and specificity of a decision rule constructed for use in the present methods will depend on the particular markers selected. Preferred sets of markers can be selected empirically using routine experimentation following the teaching herein.

Biological markers may be obtained from any host compartment, i.e., from blood, serum, urine, sputum, stool, or other biological fluid sample or tissue sample from a host or patient. The host compartment sampled will generally vary according to the marker, but the sampling should preferably be minimally invasive and easily performed by conventional techniques.

Measurement of biological markers may be carried out by any conventional techniques. Measurements of biological marker molecules may include, for example, measurements that indicate the presence, concentration, expression level, or any other value associated with a marker molecule. Various spectroscopic techniques are available for measuring biological marker molecules, including UV, visible, and infrared spectroscopies. Fluorescent labels, radioactive labels, or other readily identifiable and quantifiable labels may be used to aid in measurement of marker molecules. The expression levels of cell-bound markers can be measured by flow cytometric techniques, and the expression levels of soluble markers can be characterized by immunosorbent assay techniques.

Measurement of body temperature, respiration rate, pulse, blood pressure, or other physiological parameter markers can be achieved via clinical observation and measurement.

Monitoring

In the methods of the present invention, the patient is monitored for a period of time encompassing at least two measurements before the decision criteria are applied to the accumulated marker data. Monitoring typically involves regularly repeated measurements of the biological markers, such as a daily, hourly, or on a more frequent basis over one or more days. The time period over which markers are measured, and the frequency of measurements for each marker during the time period, will necessarily vary depending upon the presentation of the patient at the commencement of monitoring, the progression of the patient, and the particular markers selected for monitoring. In some instances, measurement of markers will occur on an hourly or more frequent basis over a part of a day, a single day, or over multiple days. The period and frequency of monitoring need not be the same for each patient or each marker. Furthermore, the period and frequency of monitoring used in model construction may differ from the period and frequency of monitoring when the decision rule derived from the model is subsequently applied to the patient marker measurements for disease detection.

The methods are useful in a clinical setting as part of the process of monitoring SIRS patients, who are at risk of developing sepsis, for the impending onset of sepsis. Thus, a patient is monitored starting from the time that the patient is first identified to be at risk, i.e., when the patient becomes SIRS-positive. Following each measurement of the patient's markers during the course of monitoring, the detection criteria of the present methods are applied to the data accumulated from both the previous and present measurements to determine if the patient has progressed to early sepsis. Monitoring is continued until either the patient is identified as exhibiting early sepsis or the monitoring is discontinued, typically because the patient is no longer SIRS-positive.

Although the methods are particularly useful for monitoring SIRS patients for the impending onset of sepsis, it will be clear that the methods may be used for patients who are considered to be, for whatever reason, enough at risk of sepsis that monitoring is warranted, even though they are not SIRS positive. Furthermore, it is recognized that the consensus definition of SIRS, used herein, may be supplanted by improved definitions in the future. It will be understood that the definition of SIRS is not a critical aspect of the invention and that the present methods will remain equally applicable.

Statistical Measures of Extreme Value

After monitoring the patient for a period of time during which two or more measurements of each marker are taken, a statistic is calculated for each marker that is a measure of extreme value of the marker over the period of time. The statistical measure of extreme value may be, for example, a measure of a maximum or minimum marker level or fitted value over a time period, a maximum or minimum increase or decrease in marker measurements or in fitted values over a time period, a maximum or minimum time spent either above or below a threshold, a maximum or minimum level of variability of measurements or fitted values from two or more time points, maximum or minimum slopes of trend lines, means of possibly discontiguous local maxima or minima, and the like. The selection of a particular statistical measure of extreme value is determined empirically, essentially as described in the examples.

Decision Rules

After a statistical measure of extreme value is derived for each marker, detection of early sepsis is carried out using a previously determined decision rule applied to the marker statistics to classify patients as positive or negative for early sepsis. The decision rule is obtained from a discrimination model, generated as described in general, below.

Model Construction

The discrimination model preferably is generated from marker data collected in a controlled study in which a population of SIRS-positive patients is monitored over time until at least one patient becomes clinically septic. The data from the subpopulation of SIRS patients who develop sepsis (converters) are compared to the data from the subpopulation of SIRS patients who do not develop sepsis (non-converters). Typically, a large number of biological markers are monitored during the controlled study, although only a subset of these markers may be used in the final decision rule. Although, in the simplest case, marker measurements from two patients, one a converter and one a non-converter, may be used to construct a discrimination model, obtaining marker measurements from a greater number of patients will generally provide a better statistical model. It will be understood that the inclusion of one or more control populations in the study may be beneficial and provide additional information useful in the generation of a discrimination model.

The present methods are used for detecting early sepsis prior to the time that clinically manifested sepsis would be either suspected or confirmed using previously described methods. Preferably, the methods detect early sepsis at least 12 hours, preferably 24 hours, prior to clinical suspicion of sepsis (predictive lead time) so that appropriate therapeutic treatment can be initiated early. For this reason, the discrimination model preferably is generated retrospectively using only data gathered from the converter patients up to a time prior to the clinical suspicion of sepsis corresponding to the desired predictive lead time. The choice of the desired predictive lead time will be based on clinical considerations; shorter or longer values may be useful depending on the clinical setting.

The biological markers monitored during the controlled study are selected from those known or suspected to be informative of the state of the immune system in response to an infection, as described above. Preferably, although not necessarily, an initial selection of these markers is carried out based on the data from the controlled study in order to identify those markers most likely to be informative in a discrimination model. This initial selection is carried out using univariate statistical tests to determine if the extreme value of the marker, considered alone, is statistically different between the converters and non-converters. Those markers that differ significantly between converters and non-converters are considered more likely to provide useful information regarding early sepsis, and are used in the subsequent generation of a multivariate discrimination model. As this is only a pre-screening procedure, the data compared may be from any time during the study, although comparing data from prior to the onset of clinically manifested sepsis in converters is preferable.

The marker measurement data obtained from the converter and non-converter subpopulations in the study are initially analyzed by calculating the marker statistics (statistical measure of extreme value) to be used in the final decision rule. The resulting values of the marker statistics are used in combination to form a multivariate discrimination model using classification or regression trees, logistic regression, log-linear discriminant analysis, discriminant analysis, neural networks, or other types of multivariate discrimination models.

Statistical software useful for multivariate discrimination modeling is well known in the art and is commercially available from a number of vendors. For example, a commercial software product useful for multivariate discrimination modeling is SPLUS® 2000 by MathSoft, Inc (Cambridge, Mass.).

The methods are useful in a variety of clinical settings as part of the process of monitoring patients who are at risk of developing sepsis. It is recognized that the distributions of marker values obtained from patients may depend on the clinical setting, such as different wards of a hospital. For example, the data provided in the examples suggest that patients admitted to the SICU following elective surgery (referred to therein as clean surgery controls) may not be entirely representative of patients entering the SICU after emergency surgery following a serious accident or coronary episode. Preferably, a model is generated from converter and non-converter data obtained from patients in the same clinical setting as in the intended use of the resulting model.

Use of the Decision Rule

Once a discrimination model has been developed with data from the controlled study, the model may be applied de novo to marker measurement data from individual patients to detect the presence of early sepsis in the patient. Typically, the decision rule produced by the discrimination model is applied iteratively during patient monitoring. The decision rule is applied anew following each measurement time-point during monitoring, based on the recalculated statistical measures of extreme value. The decision rule is re-applied after each patient measurement either until the patient is identified as having progressed to early sepsis or until the patient is discharged from medical care or is otherwise no longer considered to be at risk for sepsis. For example, in situations where a patient is in a hospital or ICU, marker measurements may be made from patient blood samples taken on a daily basis, and the model decision rule may be applied each day following the measurements. If early sepsis is detected according to the decision rule, a therapeutic treatment for the patient may be initiated or the patient may be stratified into a clinical trial. If no early sepsis is detected after monitoring the patient for several consecutive days, the patient may be discharged from the hospital or ICU.

Kits

The invention also provides kits usable for practicing the subject methods. The kits may comprise a computer readable medium, such as a CD or floppy disk, which contains programming capable of creating one or more patient data files from marker measurements taken from one or more patients considered to be at risk for sepsis, modeling time series patterns of marker measurements over the time period, extracting a statistical feature or features from the time series patterns and applying a decision rule from a discrimination model to the patient data files to determine if early sepsis is present in the one or more patients. The kits also may comprise reagents, devices and instructions for carrying out the monitoring, such as, for example, vials for patient blood sample collection or blood sample separation, staining equipment such as vials of fluorescent-labeled antibodies for selected markers, vials of lysing solution, QuantiBRITE® calibration beads for the fluorescent labels, and printed instructions for the acquisition of patient blood samples at multiple time points over a period of time, staining conditions, lysing conditions, and thresholding and gating instructions for flow cytometric measurement of the markers. In the case of soluble markers, the kit may comprise one or more solid phase "sandwich" ELISA assays with a multi-well plate, vials of solution for washing the wells, vials of labeled antibodies for the markers of interest, vials of staining solution, and printed instructions for applying marker samples to the wells, washing, applying antibodies, and staining. In turn, the kits may also comprise equipment that permits the evaluation of soluble markers with materials such as cytometric bead array products.

Utility

The methods and kits of the invention are useful in providing for detection of early sepsis in individual patients before the manifestation of overt, clinical symptoms that are observable by a physician. The early detection of sepsis may lead to decreased mortality rates for patients and reduced costs for patient treatment by permitting treatments to be focused on patients who are developing sepsis, and may result in improved clinical outcomes generally. Detection of sepsis at least 12-24 hours prior to clinical suspicion of sepsis allows for administration of antibiotic, anti-inflammatory and/or other therapeutic treatments to patients at a time wherein such treatments are potentially most beneficial.

As is typical of diagnostic methods, it is intended that the prognostic methods of the present invention represent one tool for identifying early sepsis, i.e., patients who will progress to sepsis, and that the present methods may be used in combination with additional methods. Typically, a patient will be measured and/or monitored for a number of other biological markers, including both time-varying and non-time-varying markers, such as age at time of entry into the ICU, gender, type of surgical procedure, need for mechanical ventilation, type of physiological insult, or other factor or factors useful in providing early determination of disease onset. It will be clear that a clinician typically will consider the totality of the clinical data available in making a medical judgment.

Although the primary use of the present methods will be to detect early sepsis in human patients in a hospital setting, it will be clear that the present methods can be used with non-human patients that may be at risk for sepsis, such as in a veterinary setting.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used but some experimental errors and deviations should be accounted for. Unless indicated otherwise, parts are parts by weight, molecular weight is average molecular weight, temperature is in degrees Centigrade, and pressure is at or near atmospheric. The particular discrimination models used in the following examples are exemplary, and should not be considered limiting. Various other discrimination models may also be used in accordance with the invention.

Example 1

Preferred Protocols

Measurement of Cell-Surface Markers by Flow Cytometry

Cell-surface markers, HLA-DR, CD64, and CD11b, are assayed by flow cytometry. Flow cytometry is carried out using a BD FACSCalibur™ flow cytometry system and BD FACStation™ data management system with BD FACSComp™ software, version 4.0, and BD CellQuest™ software, version 3.1.

In flow cytometric assays for a cell-surface marker, peripheral blood cells first are stained using fluorescently labeled monoclonal antibodies specific for the marker. Blood is well mixed prior to staining, and staining is carried out within four hours of the blood draw. Stained cells are kept cold and in the dark prior to data acquisition, and data acquisition is carried out within two hours of the addition of BD FACS™ Lysing Solution to the samples.

Both HLA-DR and CD64 are measured from blood collected in $K_3$EDTA collection tubes, whereas CD11b is measured in blood collected in a Na Heparin collection tube.

The results of the following assays are provided as antibodies bound per cell (AB/C). It will be clear that this is not critical, and that others quantitative measures, such as median or mean fluorescence intensity, also are useful. Expression of cell-surface markers may be measured on specific leukocyte populations, such as neutrophils or monocytes, by appropriate gating of the flow cytometric data, as is well known in the art. Preferably, for use in the present methods, HLA-DR is measured specifically on monocytes, and both CD11b and CD64 are measured specifically on neutrophils.

HLA-DR is measured using the BD QuantiBRITE™ Anti-HLA-DR PE/Anti-Monocyte PerCPCy5.5 assay (BD Biosciences, San Jose Calif.). The assay is carried out essentially as described in the product instructions, modified as follows. Samples consisting of 50 μl of blood are stained in 12×75 mm polystyrene tubes by adding 20 μl of staining reagent and incubating at room temperature (20-25° C.) for 30 minutes in the dark. Then, 0.5 ml of FACS™ Lysing Solution (BD Biosciences) is added to each tube, the tubes are vortexed at low speed for approximately one to two seconds, and incubated at room temperature for approximately five minutes in the dark.

The level of the HLA-DR expression, reported as antibodies bound per cell (AB/C), is determined as described in the product instructions (see also, e.g., U.S. Pat. No. 4,520,110 and Iyer, S B et al. BD Biosciences Application Note for QuantiBRITE™).

CD64 is measured using the BD QuantiBRITE™ CD64 PE/CD45 PerCP assay (BD Biosciences, San Jose Calif.). The assay is carried out essentially as described in the product instructions, modified as follows. Samples consisting of 50 μl of blood are stained in 12×75 mm polystyrene tubes by adding 20 μl of staining reagent and incubating at room temperature (20-25° C.) for 30 minutes in the dark. Then, 1.0 ml of FACS™ Lysing Solution (BD Biosciences) is added to each tube, the tubes are vortexed at low speed for approximately one to two seconds, and incubated at room temperature for approximately five minutes in the dark.

The level of the CD64 expression, reported as antibodies bound per cell (AB/C), is determined as described in the product instructions.

CD11b is measured using a custom-formulated CD11b (1:1) PE reagent/CD45 PerCP assay (QuantiBRITE™ PE Custom Conjugate, BD Biosciences, San Jose Calif.). The assay protocol is essentially as described for CD64, above. The level of the CD11b expression is reported as antibodies bound per cell (AB/C), as with the other cell-surface markers.

The level of TNF-R is measured as described in van der Poll et al., 1991, Journal of Leukocyte Biology, 61:156-160, incorporated herein by reference.

Measurements of Soluble Markers Using Immunosorbent Assays

For measurements of soluble markers, plasma is separated from whole blood within four hours of the blood draw time. To separate plasma, whole blood is centrifuged at 1800×g for 20 min at 4° C., after which the plasma is removed by pipette. Aliquots of approximately 225 μl of plasma are dispensed into NALGENE® cryogenic vials with color-coded caps and appropriately labeled. Vials are placed in Fisher 10×10 cryoboxes, frozen at −70° C., and kept at −70° C. until use.

Interleukin-6 (IL-6) marker is measured using the BD Pharmingen OptEIA™ Human IL-6 ELISA (Enzyme-Linked ImmunoSorbent Assay) test kit II (BD Pharmingen, San Diego, Calif.).

C-reactive protein (CRP) marker was measured using the Hemagen™ Virgo CRP 150 ELISA kit. (Hemagen Diagnostics, Inc., Waltham, Mass.).

Interleukin10 (IL-10) marker was measured using the BD Pharmingen OptEIA™ Human IL-10 ELISA test kit II.

Procalcitonin (PCT) was measured using the BRAHMS LUMItest® PCT immunoluminometric assay (ILMA) kit (BRAHMS Diagnostica, Berlin, Germany).

Example 2

Clinical Trials

Selection of SIRS Patients and Controls

Three separate patient groups and one group of normal donors were involved in the following examples. All patients were 18 years of age or older, and appropriate informed consent was obtained in all cases.

A total of 50 patients at risk for sepsis were selected from patients admitted to the Surgical Intensive Care Unit (SICU) of the Robert Wood Johnson Medical School Hospital in New Brunswick, N.J. Patients were classified as at risk for sepsis if they met two or more SIRS criteria (i.e., were SIRS positive) within a 24 hr period during their stay in the SICU.

An additional 15 patients were selected who were scheduled for clean, elective surgeries, and who were SIRS-negative at the start of monitoring, which was prior to surgery. This grou served as hospitalized controls (also referred to herein as the "clean surgical control group").

An additional group of 12 normal donor volunteers were selected. This group served as non-hospitalized controls.

Excluded from all groups were individuals with an existing suspicion of sepsis, known spinal cord injury or other condition requiring corticosteroid therapy, transplant recipients, known HIV$^+$ patients or patients otherwise identified as having known immunological abnormalities, patients with severe or extensive burns, dialysis patients, and pregnant patients. Also, individuals who progressed to sepsis within 24 hours of enrollment were excluded retrospectively from the study.

Monitoring of Subjects for Clinical Suspicion of Sepsis

Subjects in the SICU were monitored daily throughout a two week study period for clinical suspicion of sepsis. Signs and symptoms of sepsis, and the identification criteria, included the following.

Pneumonia: finding three out of four of fever, elevated white blood cell (wbc) count, productive sputum, and new infiltrate on chest radiograph.

Wound infection: finding three out of four of fever, pain, erythema, and purulent discharge.

Urinary tract infection: finding both of bacteria positive and >10 wbc/high power field.

Line sepsis: finding three out of four of fever, erythema, pain at line site, and purulence at line site.

Intra-abdominal abscess: finding all four of fever, elevated wbc, radiographic evidence of fluid collection, culture positive by aspiration or operative drainage.

The time at which clinical suspicion of sepsis was high enough to warrant both an order for cultures and institution of an empiric antibiotic regimen by the physician was defined as the "time of clinical suspicion of sepsis."

Monitoring of Vital Signs, Cell-Surface and Soluble Markers

Blood samples were drawn on a daily basis for each patient in the SICU beginning on the day that the patient was enrolled in the study and continuing for each consecutive day thereafter up to a maximum of 14 days or until the patient developed clinical suspicion of sepsis. For patients who progressed to clinical suspicion of sepsis, 3 additional consecutive blood samples were drawn, although only the pre-sepsis data were used in the model construction and testing.

Blood samples from the clean surgical control patients were taken preoperatively for one day and postoperatively for 3 consecutive days. The data from the postoperative measurements were used in the model construction and testing.

Blood samples from the normal, non-hospitalized volunteers were taken every other workday for a period of 2 consecutive weeks.

The daily blood sample draws for each patient in each group included one whole-blood draw into a $K_3$EDTA collection tube and one whole-blood draw into a Na Heparin collection tube. Blood draw times were noted, and samples were immediately placed on ice.

Each blood sample was assayed for cell-surface molecules, HLA-DR, CD64, CD11b and TNF-R; and soluble markers, IL-6, CRP, IL-10, and PCT. Cell-surface markers were measured separately on monocytes and neutrophils. Measurements were carried out essentially as described in Example 1.

Patients also were assayed for white blood cell count, body temperature, respiratory rate, and heart rate either at or close to the time of the above-described blood sample acquisition.

Example 3

Analysis of Clinical Trial Data

The data obtained from the clinical trial described in Example 2 were analyzed as described below.

The following definitions are used throughout the examples to refer to subsets of patients based on their clinical status:

Group 1: SIRS patients who never developed clinical suspicion of sepsis while in the SICU. These patients are referred to as "non-converters." Of the 50 SIRS patients in the SICU, 27 were non-converters.

Group 2: SIRS patients who developed clinical suspicion of sepsis while in the SICU. These patients are referred to as "converters." Of the 50 SIRS patients in the SICU, 23 were converters. Of the 23 converters, 20 were confirmed as septic by cultures (culture-positive sepsis) and 3 could not be confirmed by culture (culture-negative sepsis).

Group 3: The 15 patients in the clean surgical control group.

Group 4: The 12 normal donor volunteers, i.e., the non-hospitalized control group.

The number of SIRS patients in the SICU who progressed to clinical suspicion of sepsis (i.e., Group 2) is shown below for each day of SICU stay following enrollment in the study.

As noted above, patients who progressed within 24 hours of enrollment were excluded from the study.

| Day of Clinical Suspicion of Sepsis | Number of Patients |
| --- | --- |
| Day 2 | 2 |
| Day 3 | 4 |
| Day 4 | 5 |
| Day 5 | 4 |
| Day $\geq 6$ | 8 |

Extreme Values of Marker Data

The maximum or minimum of each marker, depending on the marker, were calculated for each patient other than converters over the full period the patient was monitored. For converters, the maximum or minimum of each marker were calculated for a period of time up to 1 day prior to the development of clinical suspicion of sepsis. The cutoff of one day prior to clinical suspicion of sepsis was selected because the resulting model was intended to provide predictive value of early sepsis at least one day prior to clinical suspicion of sepsis. Thus, it was appropriate to consider patient data only for the period at least one day prior to clinical suspicion of sepsis. In general, an appropriate cutoff is selected based on the intended use of the model.

For convenience in the following discussion, the quantitative measure of a marker is denoted [marker], and the maximum and minimum are denoted max[marker] and min [marker], respectively.

Initial Selection of Markers

An initial selection of markers was carried out based on the data from the controlled study in order to identify those markers most likely to be informative in a discrimination model. This initial selection was carried out using univariate statistical tests to determine if the extreme value of the marker, considered alone, was statistically different between the converters and non-converters.

The marker statistics tested that were significantly different between converters and non-converters were max[CD64] measured on neutrophils, max[CD11b] measured on neutrophils, min[HLA-DR] measured on monocytes, max[PCT], max[IL-6], max[IL-10], and max[wbc]. The markers statistics tested that were not significantly different between converters and non-converters were min[TNF-R] measured on monocytes and max[CRP]. Furthermore, max[CD64] and max[CD11b] were retrospectively assessed specifically on monocytes and found to be not significantly different between converters and non-converters.

Construction of Multivariate Discrimination Models

Multivariate discrimination models were generated from the extreme marker value statistics calculated as described above. The data from the Group 3 patients were included in the model generation. The multivariate discrimination models were evaluated for the best sensitivity and specificity for identifying patients at increased risk of sepsis prior to clinical suspicion.

Classification Tree Models

Classification tree models were generated using SPLUS® 2000 (MathSoft, Inc., Cambridge, Mass.), using the built-in tree function. The user selects the variables to be used in generating a tree model, and also indicates the maximum size of the tree. The variables to use in generating a tree model were selected from those which were found to be significantly different between converters and non-converters, as described above. The tree size was limited to 4 end (non-branching) nodes (in addition to the root node), as larger tree sizes were found to result in biologically unrealistic models or overly small partitions of the data.

Models were considered only if they were biologically reasonable. For example, a model in which a converter was identified by a value of min[HLA-DR] greater than a threshold value would not be considered farther because it is known that low levels of HLA-DR are indicative of an anti-inflammatory response.

Threshold values in a classification tree model are chosen in order to achieve the best separation of converters from the non-converters and controls, i.e., to simultaneously achieve the best sensitivity (maximize correct identification of converters) and specificity (maximize the correct identification of non-converters) possible. Typically, there is a tradeoff between sensitivity and specificity; for any given discrimination model, an increase in sensitivity results in a decrease in specificity and vice versa. It will be understood that whether the specificity or sensitivity should be first selected is a clinical decision that depends on a number of factors, such as a comparison of the possible deleterious effects of treating a non-converter for sepsis versus the risk of delaying treatment of a converter. In the present case, the models were chosen in order to achieve a pre-selected specificity level of 90%. In general, optimal model generation should be carried out in view of the desired sensitivity or specificity, as the results may depend on the sensitivity or specificity selected.

The best tree model obtained is shown below as model 1. The best model performance was obtained by measuring monocyte-associated HLA-DR, neutrophil-associated CD11b, and neutrophil-associated CD64. In order to assess the relative contribution of the various components of the best model in detecting early sepsis, the performance of the best model was compared to the performances of tree models obtained based on subsets of the three markers measured in the best model. The classification rule of the best model (model 1) is shown below, along with the classification rules of the various two-parameter and one-parameter models used in the comparisons.

1. (max[CD64]+max[CD11b])>X AND min[HLA-DR]<Y
2. max[CD11b]>X AND min[HLA-DR]<Y
3. max[CD11b]>X AND max[CD64]>Y
4. max[CD64]>X AND min[HLA-DR]<Y,
5. (max[CD64]+max[CD11b])>X,
6. min[HLA-DR]<X
7. max[CD64]>X
8. max[CD11b]>X wherein X and Y are first and second threshold values, determined independently for each model, HLA-DR is measured specifically on monocytes, and both CD11b and CD64 are measured specifically on neutrophils.

The best classification tree model provides a decision rule based on two scores. The classification tree model decision rule classifies a patient as a converter if both of the criteria are satisfied. Thus, model 1 classifies a patient as a converter if the sum of the maximum CD64 and maximum CD11b values is greater than a first threshold, and the minimum HLA-DR level is less than a second threshold.

Classification Tree Model Performance

For comparisons, a first model is considered to be superior to a second model if, for a given level of specificity, the sensitivity of the first model is greater than the sensitivity of the second model, or, for a given level of sensitivity, the specificity of the first model is greater than the specificity of the second model. As noted above, the present best model was generated in order to meet a design criterion of achieving a minimum specificity of 90%. Thus, for comparison, the performance of each of the discrimination models was determined by first selecting a specificity level and then determining the sensitivity of the model at the selected level of specificity. Although, alternatively, the performance of each of the discrimination models can be determined by first selecting a sensitivity level and then determining the specificity of the model at the selected level of sensitivity, this would be more appropriate for models designed to achieve the given sensitivity. For this reason, these alternative comparisons are not shown.

Two specificity levels, expressed as the fraction of non-converters correctly identified, were selected: 25/27 (93%) and 26/27 (96%). For each selected specificity level, the threshold values of each of the models were adjusted to achieve the given specificity while simultaneously maximizing the classification sensitivity, i.e., the fraction of converters correctly identified. Although model generation was carried out including data from the clean surgery control patients (Group 3), the specificity level discussed herein refers only to the performance classifying non-converters (Group 2). The adjustment of threshold values was done manually by inspection of a graphical representation of the data.

The sensitivities of the best classification tree decision rule and the various two-parameter and one-parameter decision rules based on subsets of the components of the best classification model are shown in the tables, below.

| Decision Rule | Sensitivity |
|---|---|
| Sensitivity of Classification Models Specificity set at 25/57 = 93% | |
| (max[CD64] + max[CD11b]) > X AND min[HLA-DR] < Y | 70% (16/23) |
| max[CD11b] > X AND min[HLA-DR] < Y | 65% (15/23) |
| max[CD11b] > X AND max[CD64] > Y | 52% (12/23) |
| max[CD64] > X AND min[HLA-DR] < Y | 39% (9/23) |
| (max[CD11b] + max[CD64]) > X | 30% (7/23) |
| min[HLA-DR] < X | 13% (3/23) |
| max[CD64] > X | 22% (5/23) |
| max[CD11b] > X | 9% (2/23) |
| Sensitivity of Classification Models Specificity set at 26/27 = 96% | |
| (max[CD64] + max[CD11b]) > X AND min[HLA-DR] < Y | 56% (13/23) |
| max[CD11b] > X AND min[HLA-DR] < Y | 52% (12/23) |
| max[CD11b] > X AND max[CD64] > Y | 43% (10/23) |
| max[CD64] > X AND min[HLA-DR] < Y | 35% (8/23) |
| (max[CD11b] + max[CD64]) > X | 13% (3/23) |
| min[HLA-DR] < X | 0% (0/23) |
| max[CD64] > X | 22% (5/23) |
| max[CD11b] > X | 9% (2/23) |

The results demonstrate that the methods of the present invention, wherein a statistical measure of extreme value over the period of time the patient has been monitored is independently derived for a plurality of markers, and the decision rule is based on the combination of resulting marker statistics, provides a decision rule with both high specificity and sensitivity.

FIG. 1 is a graphical illustration of the best-performing classification tree model decision rule applied to all patients in Groups 1-4 (77 patients). The two score components, (max [CD64]+max[CD11b]) and (min[HLA-DR]) are plotted on the vertical and horizontal axes, respectively. The region defined by the model threshold values is indicated by dotted lines. The decision rule simultaneously provides a sensitivity of 70% and a specificity of 93%, as described above. The results indicate that the decision criterion distinguished converters, i.e., patients who later progressed to sepsis, from all patients who never progress to sepsis with a high degree of accuracy.

In the specific embodiment shown in FIG. 1, a patient is classified as a converter if (max[CD64]+max[CD11b]) is greater than a threshold value of approximately 12,400 antibodies bound per cell and [HLA-DR] is less than a threshold value of approximately 9,600 antibodies bound per cell. It will be understood that the particular threshold values obtained are particular to the specific quantification methods used and the desired sensitivity and specificity of the decision rule. Changes in the assay protocol, such as the use of an alternative quantitation method, for example, would likely result in different specific threshold values.

Use of the Decision Rule

Using the decision rule generated by the classification tree model, a patient is monitored and, at each sampling time point, the two scores are calculated. Thus, using classification tree model 1, a patient is identified as exhibiting early sepsis if (max[CD64]+max[CD11b])>X and min[HLA-DR]<Y, wherein X and Y are first and second threshold values determined from the classification tree model, and the max and min are calculated based on the data collected from the start of monitoring up to and including the current time point.

Example 4

Comparison to Time-Slice Models

For comparison to the methods of the invention, classification tree models also were generated from the marker data obtained on a single day. Thus, separate classification tree models were generated for each day, and the best model for each day was selected for comparison to the models obtained using the methods of the present invention. These models that consider the data collected for a single time-point are referred to herein as "time-slice" models, as they are based on the status of the patient at a given slice in time.

Initial Selection of Markers

An initial selection of markers was carried out using univariate statistical tests to identify those markers most likely to be informative in a discrimination model. The tests were carried out essentially as described above, except that the data from each day was considered separately. The tests were carried out only for the first three days of monitoring, partly because the relevant sample size, which decreased each time a patient progressed to sepsis, became too small after day 3. The markers statistics tested that were significantly different between converters and non-converters on each day are shown below.

| Day | Markers Significant at p ≦ 0.0025 |
|---|---|
| 1 | CD11b, PCT |
| 2 | HLA-DR, CD64, CD11b, IL-10, IL-6 |
| 3 | CD64, IL-10, IL-6 |

Time-slice classification tree models were generated for each day. As noted above, statistically significant time-slice classification tree models could be determined only for the first three days of monitoring. The decision rules generated and the performance of these time-slice models, ranked according to performance, are shown in the tables, below. As described above, the desired specificity of the model was pre-selected, and, for each time-slice model tested, the threshold values were adjusted to provide the maximum sensitivity. Thus, the performance results are directly comparable to the results obtained from the classification models obtained using the methods of the present invention, provided above. To facilitate comparison, the performance of the best classification tree decision rule obtained using the methods of the present invention (designated "Model 1") is repeated in the tables, below.

| Decision Rule | Model Type | Sensitivity |
|---|---|---|
| Sensitivity of Classification Models Specificity set at 25/27 = 93% | | |
| (max[CD64] + max[CD11b]) > X AND min[HLA-DR] < Y | Model 1 | 70% (16/23) |
| [CD11b] > X AND [PCT] > Y on Day 1 | time-slice | 52% (12/23) |
| [CD64] > X AND [IL-10] > Y on Day 2 | time-slice | 48% (11/23) |
| [CD64] > X Day 3 | time-slice | 39% (9/23) |
| Sensitivity of Classification Models Specificity set at 26/27 = 96% | | |
| (max[CD64] + max[CD11b]) > X AND min[HLA-DR] < Y | Model 1 | 56% (13/23) |
| [CD11b] > X AND [PCT] > Y on Day 1 | time-slice | 43% (10/23) |
| [CD64] > X AND [IL-10] > Y on Day 2 | time-slice | 48% (11/23) |
| [CD64] > X on Day 3 | time-slice | 39% (9/23) |

Comparing the best of the classification models of the present invention to the best time-slice classification model demonstrates the improvement provided by the present invention. At 93% specificity, the model obtained by the methods of the present invention provides 70% sensitivity, whereas the best time-slice model provides only 52% sensitivity. Similarly, at 96% specificity, the model obtained by the methods of the present invention provides 56% sensitivity, whereas the best time-slice model provides only 48% sensitivity. The results demonstrate that the methods of the present invention, wherein a statistical measure of extreme value over the period of time the patient has been monitored is independently derived for each marker, and the decision rule is based on the combination of resulting marker statistics, provides significantly better overall performance than methods that are based on the values of the monitored markers obtained at a single sampling time point, as is the case, for example, in methods based on the current status of the patient.

Example 5

Discriminant Model and Logistic Regression

As an example of another applicable multivariate discrimination technique, the marker statistics were fitted to a log-linear discriminant model. Log transformations were used to produce distributions of marker values that are more Gaussian. Specifically, the data were fitted to the following log-linear discriminant model:

$$S = A*\log(\max[CD64]) + B*\log(\max[CD11b]) + C*\log(\min[HLA\text{-}DR]),$$

where A, B, and C are coefficients determined by the discriminant model.

Using the resulting model, patients are classified as converters or non-converters by comparing the S value obtained to a threshold value. Thus, based on the data from the clinical trial described above, the discriminant model produced the following decision rule for identifying early sepsis:

$$1.2*\log(\max[CD64]) + 1*\log(\max[CD11b]) - 3.0*\log(\min[HLA\text{-}DR]) > X,$$

where X is a threshold value.

As with the classification tree models, two specificity levels, expressed as the fraction of non-converters correctly identified, were selected: 25/27 (93%) and 26/27 (96%). For each selected specificity level, the threshold values of each of the models were adjusted to achieve the given specificity while simultaneously maximizing the classification sensitivity. The adjustment of threshold values was done manually by inspection. The resulting sensitivities obtained with the above log-linear discrimination model are shown below.

| Specificity | Sensitivity |
|---|---|
| 93% (25/27) | 57% (13/23) |
| 96% (26/27) | 35% (8/23) |

As with the classification tree models, the specific parameter values and threshold obtained are particular to the specific quantification methods used and the desired sensitivity and specificity of the decision rule. Changes in the assay protocol, such as the use of an alternative quantitation method, for example, would likely result in different specific threshold values.

Example 6

High Sensitivity Classification Tree

In Example 3, above, classification tree models were generated in order to achieve a pre-selected specificity level of 90%. This example described classification tree models generated in order to achieve a pre-selected sensitivity level of at least 90%. The models were generated from the same set of markers.

The best high-sensitivity tree model obtained provided the decision rule shown below.

$$\{(\max[CD64] + \max[CD11b]) > X \text{ AND } \max[CD64] > Y\}$$

OR $$\{(\max[CD64] + \max[CD11b]) < X \text{ AND } \min[HLA\text{-}DR] < Z\}$$

wherein X, Y, and Z are first, second, and third threshold values, HLA-DR is measured specifically on monocytes, and both CD11b and CD64 are measured specifically on neutrophils.

Thus, the best performance was obtained from a tree that divides the data into four subsets. The initial node subdivides patient according to their value of (max[CD64]+max[CD11b]). Then, within each subgroup, early sepsis is identified based on the value of a second marker: max[CD64] for patients with a high (max[CD64]+max[CD11b]); and min[HLA-DR] for patients with a low (max[CD64]+max[CD11b]).

The particular threshold values obtained were X=12400 AB/C, Y=1880 AB/C, and Z=7770 AB/C. As discussed above, these numeric values depend on the protocols and reagents used, and changes in the assay protocol, such as the use of an alternative quantitation method, for example, would likely result in different specific threshold values.

Performance of this high-sensitivity classification tree decision rule is shown below.

| Sensitivity | Specificity |
|---|---|
| 91% (21/23) | 70% (19/27) |

We claim:

1. A method of detecting early sepsis in a patient, wherein said method comprising the steps of:
   a) monitoring expression of markers comprising neutrophil-associated CD11b, neutrophil-associated CD64, and monocyte-associated HLA-DR over a period of time;
   b) independently deriving marker statistics comprising a maximum of said neutrophil-associated CD11b expression, a maximum of said neutrophil-associated CD64 expression, and minimum of said monocyte-associated HLA-DR expression; and
   c) applying a decision rule to the marker statistics from step (b) to detect early sepsis in said patient;
wherein said decision rule is a classification tree that detects early sepsis if
   a sum of said maximum of said neutrophil-associated CD11b expression and said maximum of said neutrophil-associated CD64 expression is greater than a first threshold value, and said minimum of said monocyte-associated HLA-DR expression is less than a second threshold value; or said decision rule is a classification tree that detects early sepsis if
   a sum of said maximum of said neutrophil-associated CD11b expression and said maximum of said neutrophil-associated CD64 expression is greater than a third threshold value, and said maximum of said neutrophil-associated CD64 expression is greater than a fourth threshold value; or
   a sum of said maximum of said neutrophil-associated CD11b expression and said maximum of said neutrophil-associated CD64 expression is less than said third threshold value, and said minimum of said monocyte-associated HLA-DR expression is less than a fifth threshold value.

2. The method of claim 1, wherein said classification tree detects early sepsis if the sum of said maximum of said neutrophil-associated CD11b expression and said maximum of said neutrophil-associated CD64 expression is greater than the first threshold value, and said minimum of said monocyte-associated HLA-DR expression is less than the second threshold value.

3. The method of claim 1, wherein said classification tree detects early sepsis if
   the sum of said maximum of said neutrophil-associated CD11b expression and said maximum of said neutrophil-associated CD64 expression is greater than the third threshold value, and said maximum of said neutrophil-associated CD64 expression is greater than the fourth threshold value; or the sum of said maximum of said neutrophil-associated CD11b expression and said maximum of said neutrophil-associated CD64 expression is less than the third threshold value, and said minimum of said monocyte-associated HLA-DR expression is less than the fifth threshold value.

* * * * *